United States Patent [19]

Shimbara

[11] Patent Number: 5,438,525
[45] Date of Patent: Aug. 1, 1995

[54] SYSTEM AND METHOD FOR THE DETECTION OF DEFECTS OF A COATING

[75] Inventor: Yoshima Shimbara, Hiroshima, Japan

[73] Assignee: Mazda Motor Corporation, Hiroshima, Japan

[21] Appl. No.: 148,261

[22] Filed: Nov. 8, 1993

[30] Foreign Application Priority Data

Nov. 9, 1992 [JP] Japan .................. 4-298356

[51] Int. Cl.⁶ ............................................. G06F 19/00
[52] U.S. Cl. .................... 364/507; 364/516;
  364/561; 364/468; 356/23.7; 378/114; 382/141;
  348/92; 348/94; 348/95; 348/125; 118/671;
  118/676; 118/695; 118/713
[58] Field of Search ............ 364/507, 550, 551.01,
  364/474.34, 474.37, 469, 468, 478, 561, 516;
  73/150 R; 356/23, 237; 378/58, 114; 382/8;
  348/86, 92, 94, 95, 125, 128, 148; 118/712–714,
  670, 671, 676, 688, 695; 209/57

[56] References Cited

U.S. PATENT DOCUMENTS

| | | | |
|---|---|---|---|
| 3,809,919 | 5/1974 | Aaron | 307/41 |
| 4,545,174 | 10/1985 | Seko | 364/561 |
| 4,831,561 | 5/1989 | Utsumi | 364/516 |
| 4,907,294 | 3/1990 | Bolton et al. | 364/507 |
| 5,040,485 | 8/1991 | Bailey et al. | 118/680 |
| 5,086,397 | 2/1992 | Schuster et al. | 364/507 |
| 5,248,341 | 9/1993 | Berry, Jr. et al. | 118/698 |

FOREIGN PATENT DOCUMENTS 62-233710 10/1987 Japan .

Primary Examiner—Emanuel T. Voeltz
Assistant Examiner—Kyle J. Choi
Attorney, Agent, or Firm—Fish & Richardson

[57] ABSTRACT

A slider is associated with a carrier for transferring a vehicle body through a magnet and an air cylinder. An amount or a distance of movement of the slider transferred together with movement of the carrier is detected with a rotary encoder and it is computed as an amount or a distance of movement of the carrier. When the carrier is transferred in a predetermined amount or distance, an image of the vehicle body is fetched by an investigating robot. The fetching does not undergo any adverse influence due to a deviation of the position of the investigating robot relative to the position of the carrier.

30 Claims, 9 Drawing Sheets

SYSTEM AND METHOD FOR THE DETECTION OF DEFECTS OF A COATING

BACKGROUND OF THE INVENTION

1. Field of the Invention

The present invention relates to a system and a method for the detection of defects or damages of a coating and, more particularly, to a system and a method for the detection of defects or damages of a coating, which involves mounting an object to be investigated onto a carrier, fetching an image of the object through an investigating robot while transferring the carrier with the object mounted thereon, and detecting such defects or damages of a coating formed on the surface of the object by processing the image of the object with an image processing means.

2. Description of the Related Art

For example, a line for the preparation or assembly of automotive vehicles has a wet rubbing sub-line for rubbing the vehicle bodies in a wet state disposed at the side downstream of a sub-line for coating the vehicle bodies with an intermediate coating paint. The wet rubbing sub-line is provided with a vehicle models detecting station at its upstream side, a coat defects detecting station at its intermediate side, and a repair station at its downstream side. The vehicle bodies are transferred at a given speed over the entire length through various stations while held with or loaded on a chain conveyor.

In the coat defects detecting station, the vehicle bodies are subject to investigation as to whether defects or damages are caused on the coating formed on their surfaces. The coat defects detecting station has an investigating robot disposed, which in turn is provided with an image pickup unit so arranged as to take an image of the surface of the coating formed on the vehicle body as an object to be investigated, for example, while transferring the investigating robot at a given speed in the direction opposite to the direction of movement of the vehicle body. An image of plural regions of the vehicle body is taken at different locations of the investigating robot.

The images taken are subjected to processing with an image processor and, when any defects or damages are to be detected on the coating formed on the vehicle body, such defects or damages are repaired in the repair station disposed on the side downstream of the coat defects detecting station. The defects or damages can be repaired with a rubbing tool mounted on the investigating robot.

For example, Japanese Patent Unexamined Publication No. 62-233,710 discloses an image pick-up unit so adapted as to take images of plural regions. This image pick-up unit can detect defects or damages of the surface of an object to be investigated, such as a coating on a vehicle body panel by radiating a laser slit light onto the surface of the coating thereon.

On the other hand, it is considered that defects or damages caused on the surface of a coating formed on the object be detected by allowing an investigating robot to fetch an image of the object while the object loaded on a carrier is transferred together with the carrier and then by subjecting the image thereof to image processing with an image processing means.

When the carrier is transferred with a conveyor or such similar device, the surging may be caused to occur due to changes of a load or due to start-up or suspension of the carrier or for other reasons. Further, a deviation may be caused between the actual position of the carrier and its position detected due to a free space between the conveyor and the carrier loaded thereon. These matters may make an actual image fetch width different in size, not constant, leading to the risk of missing investigation.

SUMMARY OF THE INVENTION

The present invention has the object to provide a system for the detection of defects or damages of or on a coating formed on an object to be investigated, so adapted as to detect an actual amount or distance of movement with high accuracy and without undergoing any adverse influence due to the surging of the carrier.

The present invention has another object to provide a method for the detection of defects or damages of or on a coating formed on an object to be investigated.

In order to achieve the object, the present invention consists of a system for the detection of defects or damages of or on a coating formed on an object to be investigated, so arranged as for an investigating robot to fetch an image of said object mounted on a carrier while transferring said carrier with said object and detect such defects or damages of a coating formed on the surface of the object by processing said image of the object with an image processing means, which comprises:

a first detection means for detecting an amount or a distance of movement of said carrier with said object mounted thereon, so arranged as to come into direct contact with said carrier; and a first control means for controlling fetch of said image of the object by said investigating robot in response to an output from said first detection means when said carrier moves in a predetermined distance.

In order to achieve the another object, a first aspect of the present invention consists of a method for the detection of defects or damages of or on a coating formed on an object to be investigated, so arranged as to mount said object on a carrier, fetch an image of said object by an investigating robot while transferring said carrier with said object mounted thereon, and detect such defects or damages of a coating formed on the surface of said object by processing said image of the object with an image processing means, which comprises:

a first step of detecting an amount or a distance of movement of said carrier with said object mounted thereon by bringing a detection means for detecting the amount or the distance of movement of said carrier into direct contact with said carrier; and a second step of fetching said image thereof by said investigating robot when a predetermined amount or distance of movement of said carrier is detected in the first step.

In order to achieve the another object, a second aspect of the present invention consists of a method for the detection of defects or damages of or on a coating formed on an object to be investigated, so arranged as to mount said object on a carrier, fetch an image of said object by an investigating robot while transferring said carrier with said object mounted thereon, and detect defects or damages of a coating formed on the surface of said object by processing said image of the object with an image processing means, which comprises:

a first step of detecting an amount or a distance of movement of said carrier with said object mounted thereon by bringing a detection means for detecting the amount or the distance of movement of said carrier into direct contact with said carrier;

a second step of fetching said image thereof by said investigating robot whenever a predetermined amount or distance of movement of said carrier is detected in the first step; and a third step of detecting said defects or damages of or on the surface of said coating by processing said image thereof fetched in the second step.

Other objects, features and advantages of the present invention will become apparent in the course of the description of the preferred embodiments, which follows, with reference to the accompanying drawings.

DESCRIPTION OF THE PREFERRED EMBODIMENTS

The present invention will be described more in detail by way of examples with reference to the accompanying drawings.

Figure 10:
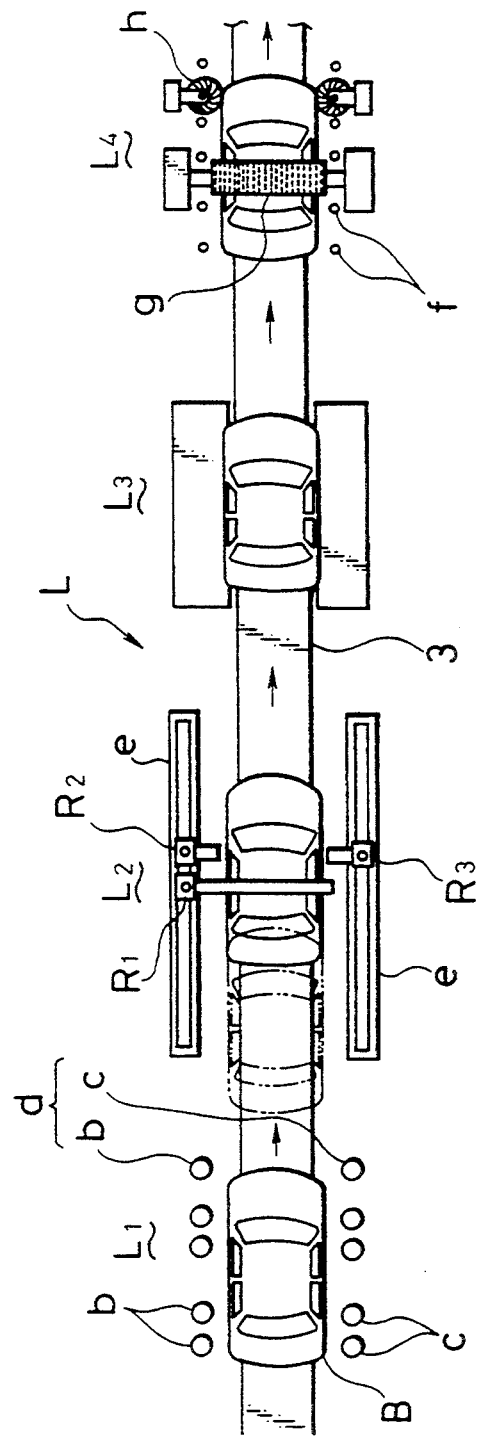
FIG. 10 is a schematic plan view showing a wet rubbing sub-line.

FIG. 10 shows a wet rubbing sub-line disposed at the side downstream of an intermediate coating sub-line L in a vehicle bodies production line.

The wet rubbing sub-line L comprises a vehicle models detecting station L1 disposed at its upstream side, a coat defects detecting station L2 disposed at its intermediate upstream side, a repair station L3 disposed at its intermediate downstream side, and a water-washing station L4 at its downstream side. After coating vehicle bodies B with an intermediate paint, they are transferred to a carrier (not shown) so arranged as to move with a chain conveyor disposed in the wet rubbing sub-line L so as to move at a given speed over the entire length through various stations. In FIG. 10, reference numeral 3 denotes a railway on which the carriers are to be moved with the vehicle bodies B mounted thereon.

The vehicle models detecting station L1 is provided with a plurality of sensors d for detecting models of vehicle bodies B, each of which comprises a light emitting section b and a light receiving section c.

The coat defects detecting station L2 has at least two bases e and e disposed on the respectively left and right sides, when viewed from the downstream side, along or parallel to the railway 3, on which the vehicle bodies B are being transferred through the wet rubbing sub-line. At the base e disposed on the left side of the railway 3, there are mounted a first robot R1 and a second robot R2, each being of the orthogonally coordinate type. At the base e disposed on the right side of the railway 3, there is mounted a third robot R3 of the orthogonally coordinate type. The first investigating robot R1 is provided with an image pick-up unit for taking an image of plural regions preset at plural regions such as, for example, a bonnet, a roof and a trunk lid of a vehicle body B and with a rubbing tool for rubbing off damaged areas of a coating in the region to be pictured with the image pick-up unit to thereby repair defects or damages of or on the coating. The second investigating robot R2 is provided with an image pick-up unit for taking an image of plural regions preset at plural regions such as, for example, a left front fender, a left side door and a left rear fender of the vehicle body B and with a rubbing tool for rubbing off damaged areas of a coating in the region to be pictured with the image pick-up unit to thereby repair defects or damages of or on the coating. The third investigating robot R3 is provided with an image pick-up unit for taking an image of plural regions preset at plural regions such as, for example, a right front fender, a right side door and a right rear fender of the vehicle body B and with a rubbing tool for rubbing off damaged areas of a coating in the region to be pictured with the image pick-up unit to thereby repair defects or damages of or on the coating.

The image of each of the plural regions is taken with the respective image pick-up unit while each of the first investigating robot R1, the second investigating robot R2 and the third investigating robot R3 is being transferred at a predetermined speed in the direction opposite to the direction of movement of the vehicle bodies B. Each of the image pick-up units mounted on each of the respective robots R1, R2 and R3 is so arranged as to take an image of the plural regions preset on the vehicle body B at a predetermined timing. The image signals are then processed and, whenever such defects or damages to be repaired are detected from an image data, the robot disposed at the location in the region corresponding to such defects or damages is immediately allowed to move in synchronization with the vehicle body B in the direction along or parallel to the direction of movement of the carrier with the vehicle body B mounted thereon and such defects or damages are to be repaired with the rubbing tool mounted on the respective robot.

The repair station L3 is disposed in order to repair such defects or damages manually by an operator as incapable of being repaired with the investigating robots R1, R2 and R3.

The water-washing station L4 is arranged and adapted to wash the vehicle body B with water showers f, g and h, after the body B has been repaired in the previous stations L2 and L3.

It can be noted that, in FIG. 10, each of the investigating robots R1, R2 and R3 can be set in a fixed manner as will be described hereinafter. In this case, however, each of the investigating robots R1, R2 and R3 may be provided with an image pick-up unit, without any rubbing tool for repairing such defects or damages detected with the image pick-up unit mounted on the respective investigating robot and such defects or damages are to be repaired in a station of the line L, which follows the coat defects detecting station L2.

A detailed description will now be made of an example of the coat defects detecting station L2 with reference to FIGS. 1 to 7. In this example, the station L2 is provided with investigating robots R, each corresponding to the investigating robots R1, R2 and R3, which are each of the fixed type and each of which is arranged exclusively for taking an image of the regions preset on the vehicle body B.

Figure 1:
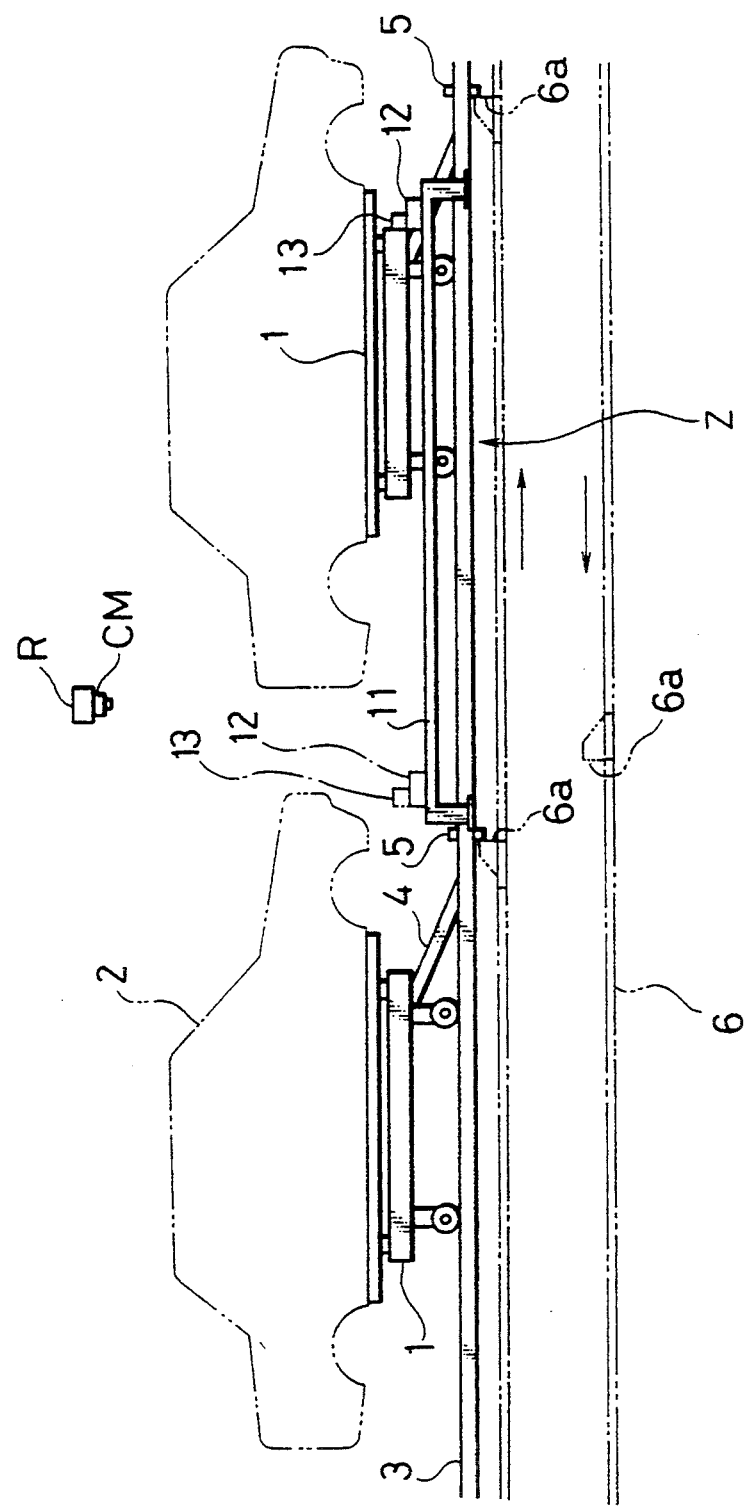
FIG. 1 is a plan view showing the structure of a means for following the synchronous movement of the carrier.
Figure 2:
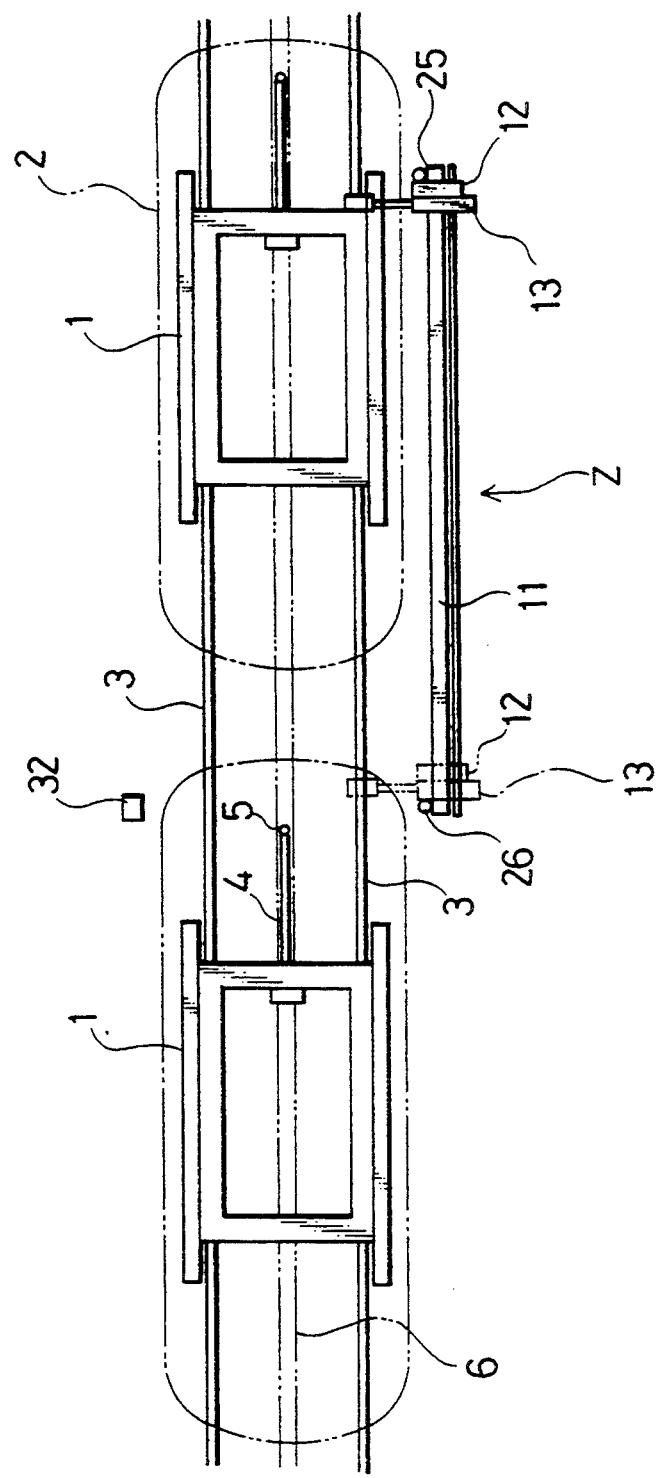
FIG. 2 is a side view of FIG. 1.

As shown in FIGS. 1 and 2, a carrier 1 is loaded with a vehicle body 2 and the carrier 1 is transferred on and along a railway 3. The carrier is provided with a projecting member 4 disposed projecting forward and downward from the bottom portion of a body of the carrier 1. The projecting member 4 is provided at its top end with an engagement pin 5 extending vertically so as to be engaged with the engagement portion 6a of a conveyor 6 for transferring the vehicle bodies 2. The carriers 1 can be transferred by driving the conveyor 6.

Figure 3:
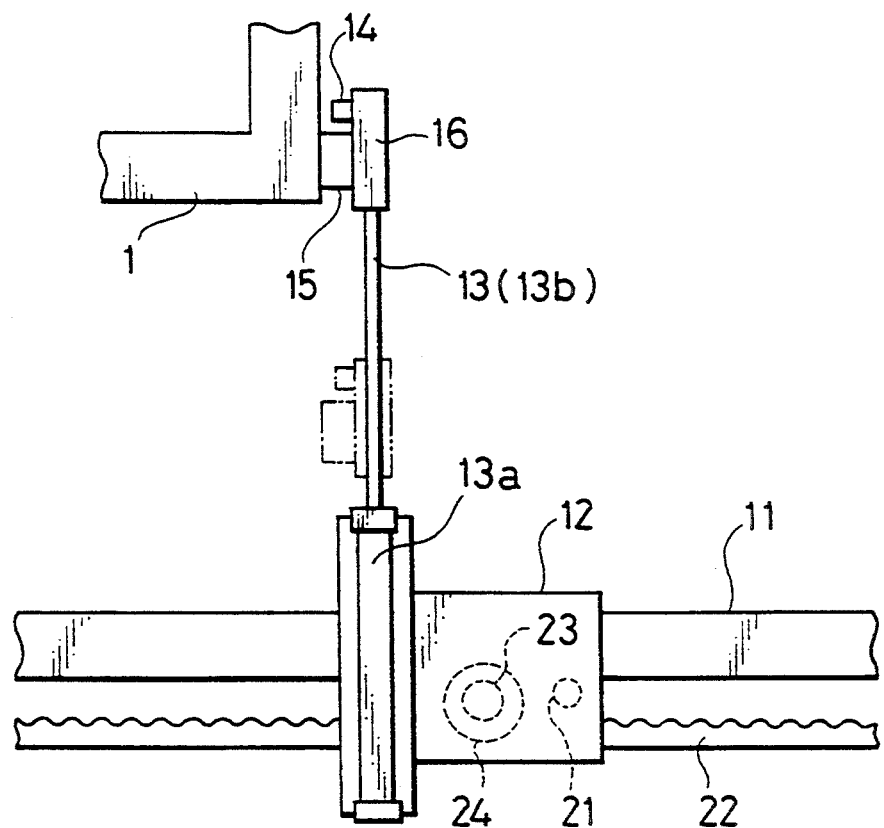
FIG. 3 is a schematic front view for describing the detection of the position of the vehicle body or the carrier during continuous transfer of the vehicle bodies or the carriers.
Figure 4:
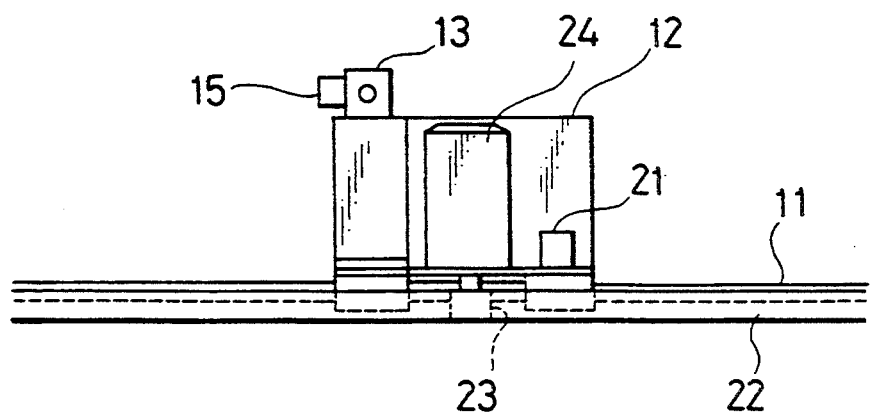
FIG. 4 is a schematic plan view of FIG. 3.

The vehicle bodies production line is disposed on its side along or parallel to a robot-working zone Z in which a railway member 11 is disposed along or parallel to the railway 3. The railway member 11 is slidably mounted with a slider 12. As shown in FIGS. 3 and 4, the slider 12 has an air cylinder 13 comprising a cylinder body 13a and a piston rod 13b. The air cylinder 13 is arranged so as for its axis to intersect with the direction in which the railway 3 extends and the piston rod 13b is so arranged as to extend toward the side where the railway 3 is disposed. As shown specifically in FIGS. 3 and 4, the piston rod 13b is provided at its top end portion with an attachment unit 16 that in turn has a non-contact switch 14 for detecting the carrier 1 and a magnet means 15 which can be brought into contact with the carrier and which in turn attracts the carrier 1.

The slider 12 is provided with a rotary encoder 21 for detecting an amount or a distance of movement of the carrier 1 on and along the railway member 11 and with a motor 24 for returning the slider 12 to its original position by rotating a pinion 23 in mesh with a rack bar 22 extending along and parallel to the railway member 11. Further, as specifically shown in FIG. 2, the railway member 11 has a non-contact switch 25 disposed at its front portion for detecting a limit of its length in which the slider 12 can follow and move in synchronization with the movement of the carrier 1 and a non-contact switch 26 disposed at its rear portion for detecting a limit of its length in which the slider 12 can be returned to its original position.

The rotary encoder 21 is so arranged as to generate a number of pulses in proportion to the number of rotation of the slider 12 while being rotated on and along the railway member 11 when the slider 12 is being transferred from the rear portion of the railway member 11 to the front portion thereof. The rotary encoder 21 may be of the type in which its rotator is of the pinion type or in which its rotator is of the roller type. The rotary encoder 21 can be rotated in proportion to the amount or length of movement of the slider 12, for example, by engaging the rotator of the rotary encoder 21 with a rack 22 in the case of the rotary encoder of the pinion type, on the one hand, and by pressing the rotator of the rotary encoder 21 upon and in contact with a flat surface of the railway member 11 in the case of the rotary encoder of the roller type, on the other hand.

Figure 5:
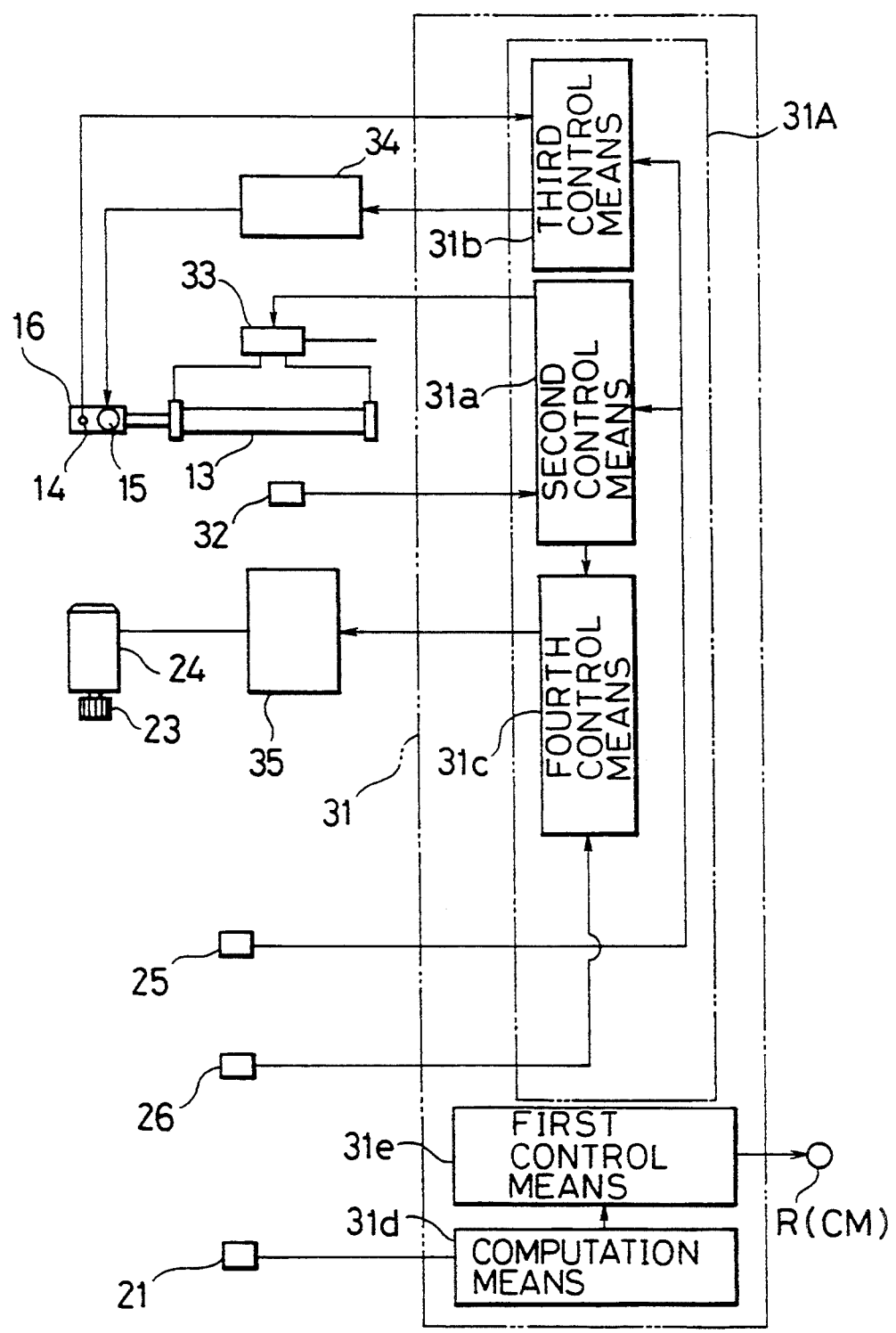
FIG. 5 is a block diagram showing the control system of the means for following the synchronous movement of the carrier.

As shown in FIG. 5, a controller 31 has an air cylinder control means 31a as a second control means and a magnet control means 31b as a third means. The air cylinder control means 31a is so arranged as to extend or expand an air cylinder 13 by controlling a control valve 33 in response to a signal from a non-contact switch 32 disposed between the left and right rails of the railway 3 for detecting arrival of the vehicle body B at a predetermined position of the railway 3. The magnet control means 31b is so arranged as to generate signals for exciting the magnet to a magnet-exciting section 34 in response to an output from the non-contact switch 14. On the other hand, the magnet control means 31b is arranged to provide the magnet-exciting section 34 with signals for cutting the generation of the magnet-exciting signals when the non-contact switch 25 generates its output signals, while the air cylinder control means 31a is arranged to contract the air cylinder 13 by controlling the control valve 33. The controller 31 is further provided with a motor drive control means 31c as a fourth control means, which is so arranged as to drive the motor 24 by providing a motor control section 35 with drive signals in response to signals for contracting the air cylinder 13 from the air cylinder control means 31a and to suspend the rotation of the motor 24 by providing the motor control section 35 with signals for suspending the rotation of the motor 24 in response to a signal from the non-contact switch 26. The air cylinder control means 31a, the magnet control means 31b and the motor drive control means 31c constitute a controller section 31A for controlling the synchronous movement of the slider 12 with the carrier 1.

Figure 6:
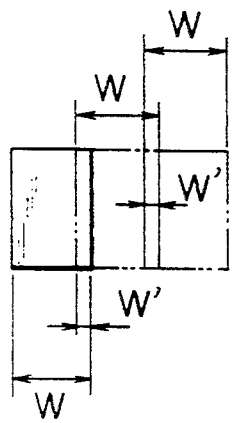
FIG. 6 is a schematic illustration of an image fetch width of an image of an object to be investigated.

Further, the controller 31 has a computation means 31d and an image fetch control means 31e as a first control means; the computation means 31d being provided for computing an amount or a distance of movement of the carrier 1 in response to signals from the rotary encoder 21 during the period during which the carrier 1 is being transferred in the robot-working zone Z and the first control means 31e being provided for having an investigating robot R with an image pick-up unit CM fetch an image of the vehicle body B in response to signals from the computation means 31d whenever the carrier 1 has been transferred in a predetermined amount or distance of the railway 3. The investigating robot R is arranged and associated with an image processor (not shown) as an image processing means so as to fetch the image in a predetermined image fetch width W (with an overlap width W'), as shown in FIG. 6, and to detect defects or damages on a coating of the object to be investigated by subjecting the image to image processing with the image processing means.

Figure 7:
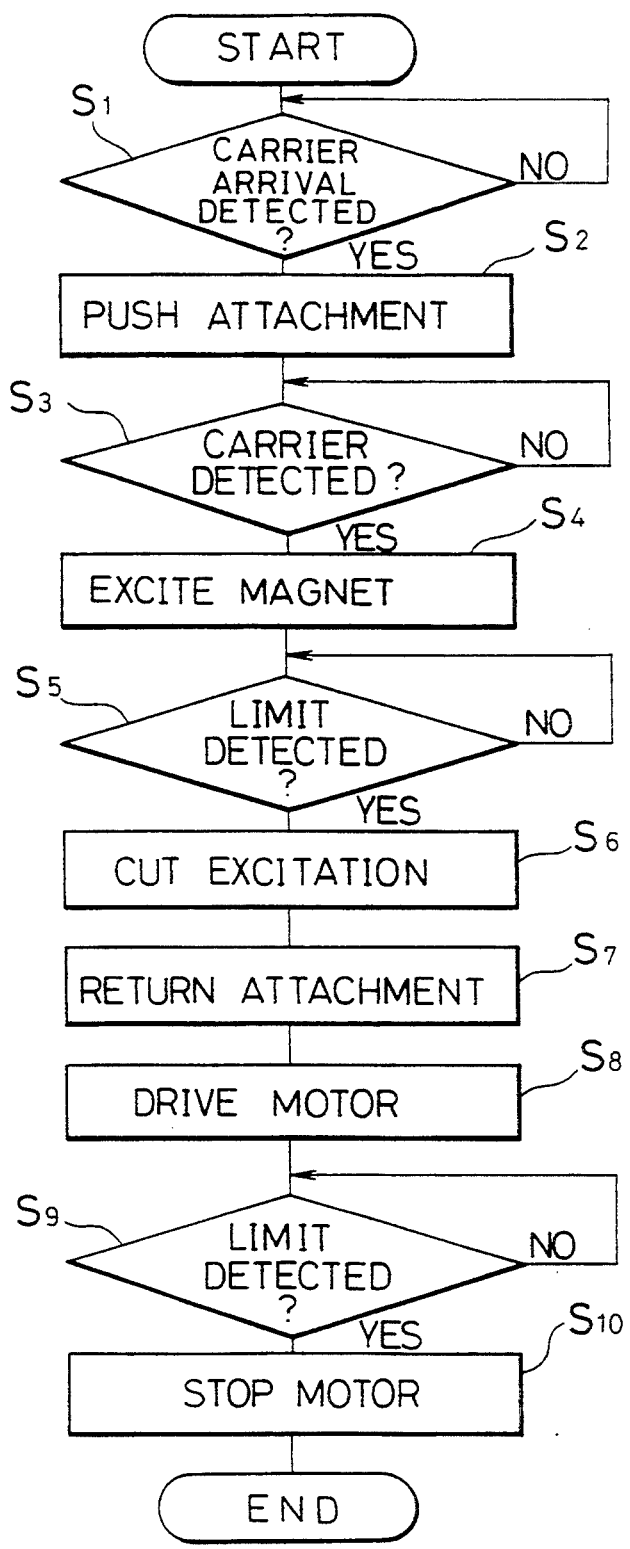
FIG. 7 is a flow chart showing the processes of the control for detecting the position of the vehicle body or the carrier.

Further, a series of the processing for detecting the position of the carrier 1 will be described with reference to FIG. 7.

First, at step S1, a decision is made to determine from a signal from the non-contact switch 32 if the carrier 1 has arrived at a predetermined position of the railway 3. When the decision at step S1 gives an affirmative answer, on the one hand, then the program flow goes to step S2 at which the air cylinder 13 is operated pushing the attachment unit 16 forward to thereby come into direct contact with the carrier 1. On the other hand, when it is decided at step S1 that the carrier 1 has not yet arrived at the predetermined position of the railway 3, then decision at step S1 has been repeated until the carrier 1 with the vehicle body B mounted thereon arrives.

After the attachment unit 16 has been pushed forward at step S2, then a decision is further made at step S3 to determine if the carrier 1 enters and is located at a predetermined position of the railway 3 from a signal from the non-contact switch 14. When it is decided at step S3 that the carrier 1 is located in the predetermined position of the railway 3, on the one hand, then the program flow goes to step S4 at which the magnet means 15 is excited to thereby attract the carrier 1. When the decision at step S3 indicates that no carrier 1 exists in the predetermined position thereof, on the other hand, then the program flow returns to step S3, thereby repeating the process at step S3 until the carrier 1 is detected at its predetermined location of the railway 3. As the magnet means 15 is excited, the magnet means 15 is allowed to come into direct contact with the carrier 1 attracting the carrier 1, thereby securing the movement of the slider 12 through the air cylinder 13 in synchronization with the movement of the carrier 1.

Then, at step S5, it is decided to determine on the basis of a signal from the non-contact switch 25 if the slider 12, or the carrier 1, has arrived at a predetermined limit of its synchronous movement. When decision at step S5 indicates that the slider 12 has reached its limit, on the one hand, then the program flow goes to step S6 at which the excitation of the magnet means 15 is suspended and then to step S7 at which the air cylinder 13 is caused to contract and the attachment unit 16 is returned to its original position. When it is decided at step S5 that the slider 12 does not yet reach its limit of movement, on the other hand, the decision at step S5 is repeated until the slider 12 arrives at its predetermined limit of movement. During the period of time when the decision at step S5 has been repeated, the process of having the investigating robot fetch the image of the vehicle body B is effected in order to detect the defects or damages of or on the coating formed on the vehicle body B.

After the attachment unit 16 has been returned to its original position at step S7, the motor 24 is driven through the motor control section 35 at step S8, followed by step S9 at which a decision is made to determine on the basis of a signal from the non-contact switch 26 if the slider 12 has returned to its predetermined return limit of movement.

When it is decided at step S9 that the slider 12 has returned its return limit of movement, on the one hand, then the program flow goes to step S10 at which the motor 24 is suspended. When the decision at step S9 gives a negative result, on the other hand, the process at step S9 is repeated until the slider 12 arrives at its return limit of movement.

Although the magnet means is employed for the attachment means in the first embodiment of the invention, there is no restriction of the attachment means to the magnet means and there may be employed any attachment means capable of coming into direct contact with the carrier 1, such as an attaching pad.

As described hereinabove, the first embodiment of the present invention is so adapted as to detect an amount or a distance of movement of the carrier 1 by bringing the slider 12 serving as the means for detecting an amount or distance of carrier movement into direct contact with the carrier 1 and fetch an image of the vehicle body loaded on the carrier 1 by the investigating robot R when the carrier 1 is transferred in a predetermined amount or distance of movement. Hence, the system according to the embodiment of the present invention can detect defects or damages on the surface of the coating formed on the vehicle body B without undergoing a deviation in the location of the investigating robot R relative to the location of the carrier 1.

Figure 8:
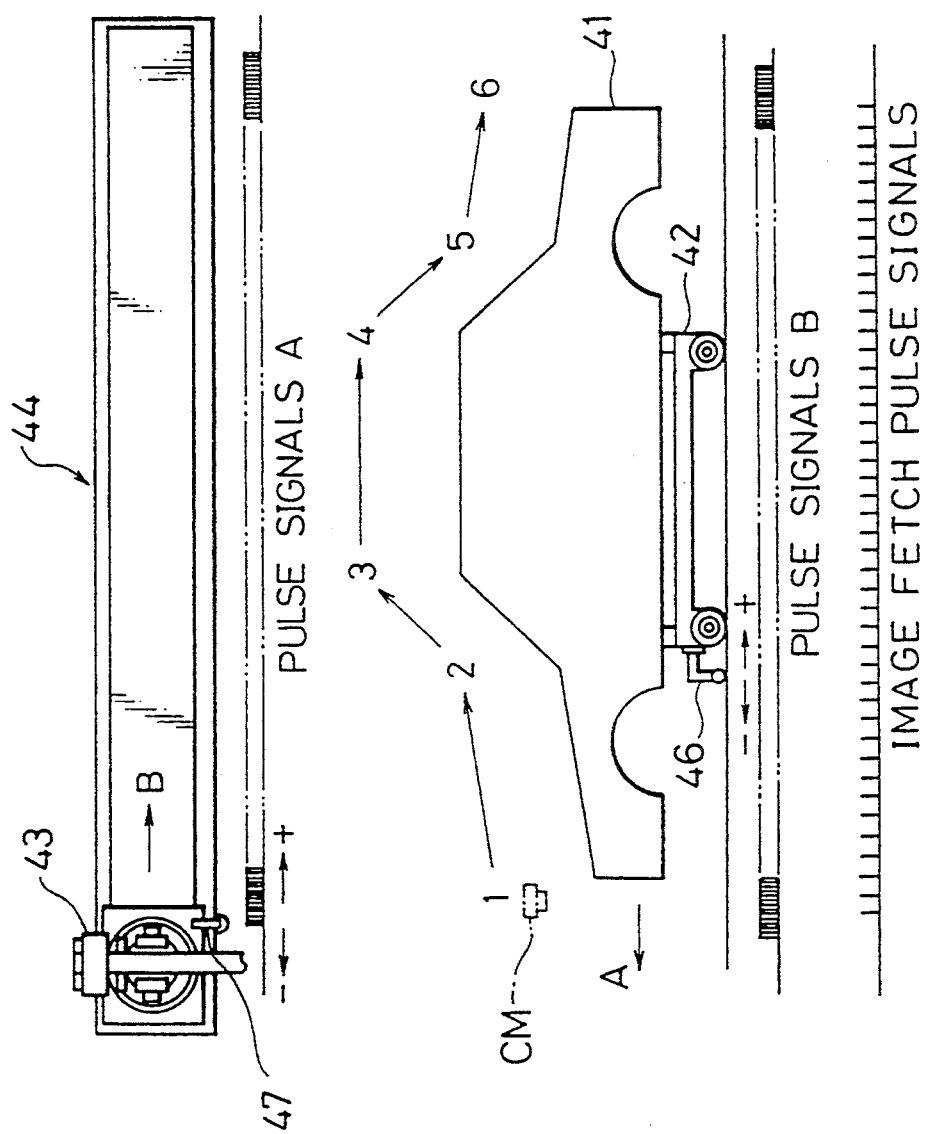
FIG. 8 is a schematic illustration showing a high-speed pick-up system during the continuous transfer of vehicle bodies.
Figure 9:
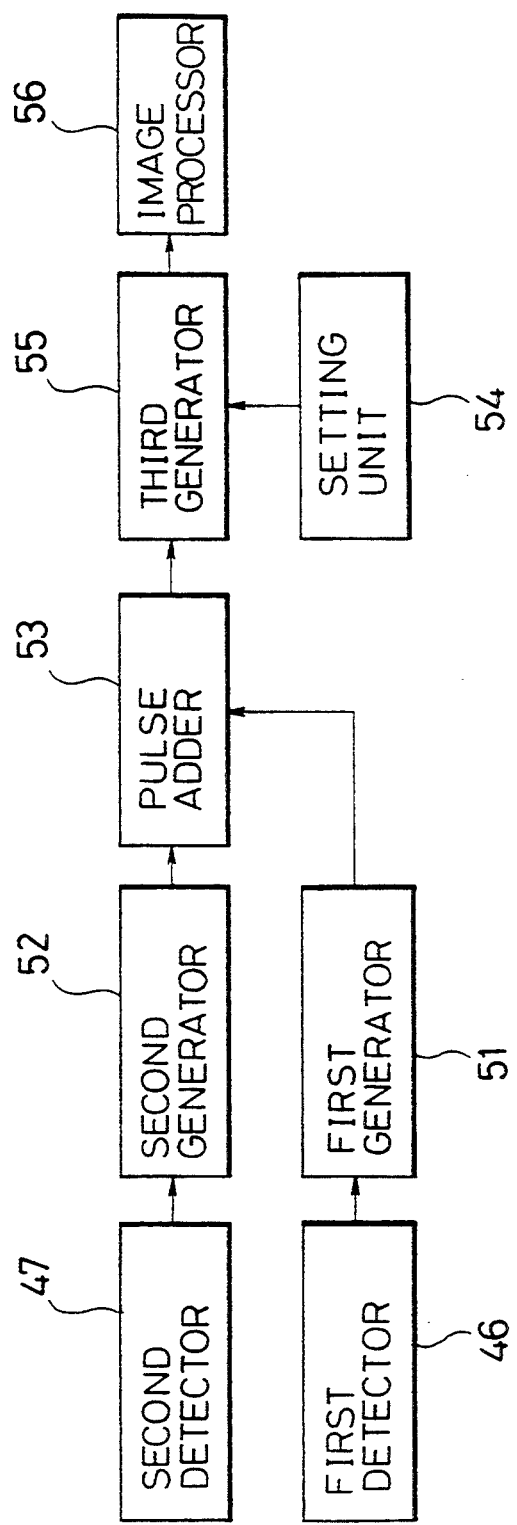
FIG. 9 is a block diagram showing the control system for the high-speed pick-up system.

Referring now to FIGS. 8 and 9, a description will be made of a second embodiment of the present invention, which is directed to an example in which an investigating robot means is so arranged as to move relative to the movement of the carrier.

As shown in FIG. 8, a carrier 42 with a vehicle body 41 is transferred with a chain conveyor or other conveyor means in the direction as indicated by reference symbol "A" and an investigating robot 43, corresponding to the investigating robot R1, R2 or R3, is so arranged as to move with a robot-operating device 44 in the direction, as indicated by reference symbol "B", opposite to the direction A. The carrier 42 has a first detector 46 for detecting an amount or a distance of movement of the carrier 42, and the investigating robot 43 has a second detector 47 for detecting an amount or a distance of movement of the investigating robot 43. In FIG. 8, the arrows connected between encircled reference numerals 1-2, 2-3, 3-4, 4-5, and 5-6 denote each the imaginary line of movement of the investigating robot 43, specifically, the line of movement of the image pick-up unit mounted to the investigating robot 43.

FIG. 9 shows the control system for controlling the movement of the carrier 42 and the investigating robot 43. Signals are transmitted from the first detector 46 to a first generator 51 which in turn generates pulse signals B indicative of a constant-distance transfer of the carrier 42. On the other hand, the second detector 47 generates signals to a second generator 52 which in turn generates pulse signals A indicative of a constant-distance transfer of the investigating robot.

The first detector 46 and the second detector 47 may be comprised each of a rotary encoder. The first detector 46 comprised of the rotary encoder may have its rotator disposed so as to come into contact with the railway 3 or to be engaged with a rack arranged in the railway 3, as shown in FIGS. 1 to 3. On the other hand, the second detector 47 comprised of the rotary encoder may have its rotator disposed so as to come into contact with a railway on and along which the investigating robot 43 moves or with a rack arranged in such railway.

The pulse signals generated from both of the first and second generators 51 and 52 are transmitted to a pulse adder 53 by which they are added. The resulting signals are then transmitted to a third generator 55 for generating pulse signals for fetching an image of the object to be investigated. To the third generator 55 are transmitted signals generated from a setting unit 54 for setting an image fetch width. Then, the third generator 55 gives image fetch pulse signals to an image processor 56. Thus, the image processor 56 allows the investigating robot 43 to fetch the image of the object such as the vehicle body 41 by the image fetch width set by the setting unit 54.

As described hereinabove, in the second embodiment of the present invention in which the investigating robot 43 is arranged to move, the first control means for controlling the fetch of the image of the object such as, for example, the vehicle bodies, are supplied with the output from the second detection means, indicative of the amount of the distance of movement of the investigating robot 43, in addition to the output from the first detection means, indicative of the amount or the distance of movement of the carrier 42. The image of the object is fetched by the investigating robot 43 when the sum of the amounts or the distances of the first and second detection means becomes the predetermined value. Hence, defects or damages of the coating formed on the object can be detected with high accuracy without undergoing any adverse influence due to a deviation of the position of the investigating robot 43 relative to the position of the carrier 42.

The present invention is not intended in any manner to be limited to the embodiments as described hereinabove, and it is to be understood that any variations and modifications made so as not to deviate from the basic concept of the present invention are interpreted as being contained within the scope and the spirit of the invention.

What is claimed is:

1. A system for the detection of defects or damages of or on a coating formed on an object to be investigated, so arranged as for an investigating robot to fetch an image of said object mounted on a carrier while said carrier with said object is being transferred and detect such defects or damages of a coating formed on the surface of the object by processing said image of the object with an image processing means, comprising:
    a first detection means for detecting an amount or a distance of movement of said carrier with said object mounted thereon, so arranged as to come into direct contact with said carrier; and
    a first control means for controlling fetch of said image of the object by said investigating robot in response to an output from said first detection means when said carrier moves in a predetermined distance.

2. A system as claimed in claim 1, wherein:
    said investigating robot is so disposed as to be movable in a direction of movement of said carrier;
    a second detection means for detecting an amount or a distance of movement of said investigating robot means; and
    said first control means is so adapted as for said investigating robot means to fetch said image of the object in proportion to output from said first detection means and output from said second detection means.

3. A system as claimed in claim 2, wherein said first control means is so adapted as for said investigating robot to fetch said image of the object when the sum of the amount or the distance of movement of said carrier detected by said first detection means and the amount or the distance of movement of said investigating robot detected by said second detection means becomes equal to or larger than a predetermined value.

4. A system as claimed in claim 1, wherein:
    said first detection means has a bar member disposed projecting toward said carrier; and
    said bar member is so disposed as to allow said first detection means to come into direct contact with said carrier and to attract said carrier through an attachment means.

5. A system as claimed in claim 4, wherein said attachment means comprises a magnet.

6. A system as claimed in claim 4, wherein:
    said bar member is so arranged as to be extendible toward said carrier or contractible from said carrier; and
    said bar member is disposed in a position in which said bar member is projected toward said carrier when said carrier is located in a predetermined position of a working zone.

7. A system as claimed in claim 6, wherein:
    said bar member has a carrier detecting means for detecting said carrier in a position of a railway on which said carrier is transferred; and
    said attachment means is so adapted as to operate when said carrier is detected by said carrier detecting means as being located in the predetermined position of said railway.

8. A system as claimed in claim 6, wherein said bar member comprises a cylinder means.

9. A system as claimed in claim 4, wherein:
    said bar member is so arranged as to be movable back and forth along or parallel to movement of said carrier; and
    said first detection means is so adapted as to detect an amount or a distance of movement of said bar member parallel to a direction of movement of said carrier.

10. A system as claimed in claim 9, wherein said first detection means comprises a rotary encoder.

11. A system as claimed in claim 4, wherein:
    a guide means is disposed in a direction of movement of said carrier;
    a slider is held with said guide means so as to be movable back and forth;
    said bar member is mounted to said slider; and
    a drive means is further provided for returning said slider to its original position.

12. A system as claimed in claim 11, wherein:
    said drive means comprises:
    a rack disposed along said guide means; and
    a motor mounted to said slider for driving a pinion in mesh with said rack.

13. A system as claimed in claim 11, wherein:
    said slider is provided with a front-end-position detecting means for detecting a front end position of said slider, which corresponds to a forward stroke end of said slider and which is located at its front end position of said slider opposite to an original end position thereof; and
    said drive means is so arranged as to return said slider to its original end position when it is detected by said front-end-position detecting means that said slider is located at its forward stroke end.

14. A system as claimed in claim 13, wherein:
    said slider is provided with a return detecting means for detecting return of said slider to its original end position; and
    said drive means is so arranged as to be suspended when it is detected by said return detecting means that said slider is returned to its original end position.

15. A system as claimed in claim 1, wherein said investigating robot means is of a fixed type.

16. A system as claimed in claim 1, wherein said investigating robot is of such a type as capable of moving back and forth along a direction of movement of said carrier.

17. A system as claimed in claim 16, wherein said first control means is so adapted as for said investigating robot to fetch said image of the object while said investigating robot is moved in a direction opposite to the direction of movement of said carrier.

18. A system as claimed in claim 17, further comprising:
    a second detection means for detecting an amount or a distance of movement of said investigating robot; and said first control means is so adapted as for said investigating robot to fetch said image of the object when the sum of the amount or the distance of movement of said investigating robot means detected by said second detection means and the amount or the distance of movement of said carrier detected by said first detection means becomes equal to or larger than a predetermined value.

19. A system as claimed in claim 18, wherein:
said first detection means comprises a unit of such a type as capable of generating a pulse in proportion to movement of said carrier; and
said second detection means comprises a unit of such a type as capable of generating a pulse in proportion to movement of said investigating robot.

20. A system as claimed in claim 1, wherein:
said first detection means comprises a movement member;
said movement member is so arranged as to select a contact status in which said first detection means is in direct contact with said carrier and a detached status in which said first detection means is detached from said carrier;
said movement member is arranged to move together with said carrier in its said contact status; and
an amount or a distance of movement of said movement member in its said contact status along a railway on and along which said carrier moves is set as an amount or a distance of movement of said carrier to be detected by said first detection means.

21. A system as claimed in claim 1, wherein:
said first detection means has a movement member fixed to or on said carrier; and
an amount or a distance of movement of said movement member along a railway on and along which said carrier moves is set as an amount or a distance of movement of said carrier detected by said first detection means.

22. A system as claimed in claim 1, wherein an image fetch width of an image of the object to be currently fetched by said first control means is so set as to partially overlap with an image thereof previously fetched.

23. A system as claimed in claim 1, wherein:
said carrier is engaged with a conveyor means disposed along or parallel to a direction of movement of said carrier; and
said carrier is transferred by driving said conveyor means.

24. A system as claimed in claim 23, wherein:
said conveyor means comprises a chain conveyor;
said chain conveyor is provided with an engagement member;
said carrier is provided with an engagement pin engageable with said engagement member of said chain conveyor; and
said carrier is transferred with said chain conveyor by driving said chain conveyor, in such a state in which said engagement member of said chain conveyor is engaged with said engagement pin of said carrier.

25. A system as claimed in claim 1, wherein said object to be investigated comprises a coated vehicle body.

26. A system as claimed in claim 25, wherein said investigating robot is so disposed as to investigate defects or damages on at least an upper surface of said vehicle body and one of a left side surface and a right side surface thereof.

27. A system as claimed in claim 25, wherein said investigating robot comprises a first investigating robot for detecting defects or damages on the upper surface of said vehicle body, a second investigating robot for detecting defects or damages on the left side surface thereof, and a third investigating robot for detecting defects or damages on the right side surface thereof.

28. A method for the detection of defects or damages of or on a coating formed on an object to be investigated, so arranged as to mount said object on a carrier, fetch an image of said object by an investigating robot while transferring said carrier with said object mounted thereon, and detect defects or damages of a coating formed on the surface of said object by processing said image of the object with an image processing means, comprising:
a first step of detecting an amount or a distance of movement of said carrier with said object mounted thereon by bringing a detection means for detecting the amount or the distance of movement of said carrier into direct contact with said carrier; and
a second step of fetching said image thereof by said investigating robot when a predetermined amount or distance of movement of said carrier is detected in the first step.

29. A method for the detection of defects or damages of or on a coating formed on an object to be investigated, so arranged as to mount said object on a carrier, fetch an image of said object by an investigating robot while transferring said carrier with said object mounted thereon, and detect defects or damages of a coating formed on the surface of said object by processing said image of the object with an image processing means, comprising:
a first step of detecting an amount or a distance of movement of said carrier with said object mounted thereon by bringing a detection means for detecting an amount or a distance of movement of said carrier into direct contact with said carrier;
a second step of fetching said image thereof by said investigating robot whenever a predetermined amount or distance of movement of said carrier is detected in the first step; and
a third step of detecting said defects or damages of or on the surface of said coating by processing said image thereof fetched in the second step.

30. A method as claimed in claim 29, wherein said predetermined value is set as a length of an image to be currently fetched in the second step, which partially overlaps with said image previously fetched.

* * * * *